United States Patent [19]

Achari

[11] 4,237,722
[45] Dec. 9, 1980

[54] EXHAUST GAS SENSOR ELECTRODE IMPROVEMENT

[75] Inventor: Achyuta Achari, Detroit, Mich.

[73] Assignee: Ford Motor Company, Dearborn, Mich.

[21] Appl. No.: 5,419

[22] Filed: Jan. 22, 1979

[51] Int. Cl.³ ............................................. G01N 27/12
[52] U.S. Cl. ...................................... 73/23; 338/34
[58] Field of Search ................... 73/23, 27 R; 338/34; 422/98

[56] References Cited

U.S. PATENT DOCUMENTS

| 3,886,785 | 6/1975 | Stadler et al. | 73/23 |
| 3,932,246 | 1/1976 | Stadler et al. | 73/27 R |
| 4,033,169 | 7/1977 | Fujishiro et al. | 73/23 |

FOREIGN PATENT DOCUMENTS 2062574  7/1971  Fed. Rep. of Germany ............. 338/34

*Primary Examiner*—Stephen A. Kreitman
*Attorney, Agent, or Firm*—Clifford L. Sadler

[57] ABSTRACT

An improved exhaust gas sensor for use in sensing the partial pressure of oxygen in the exhaust gases from an internal combustion engine. The sensor has a titania ceramic element in which two electrodes are embedded. The electrodes in the past have been made from pure platinum, this precious metal being required to enable the sensor electrodes to survive at temperatures up to about 900° C. in the hostile gaseous environment. Even with the use of this platinum electrode material, electrode failures have occurred. These now have been found to be caused by the formation of platinum carbide from the chemical reaction of the platinum electrode material with exhaust gas constituents. Also, Pt loss has occurred from oxidation thereof and vaporization of the oxide. It has been found that deterioration of sensor electrodes may be prevented by forming these electrodes from an alloy consisting essentially of platinum and another material having a lower vapor pressure and lower surface tension than platinum. Specifically, an alloy consisting essentially of platinum and another metal selected from the group consisting of gold and rhodium may be used. An alloy of platinum and gold is preferred. Annealing the titania element electrodes functions, as does the alloy formation, as a means for increasing the magnitude of the energy required for reaction of the Pt with carbon or oxygen.

12 Claims, 14 Drawing Figures

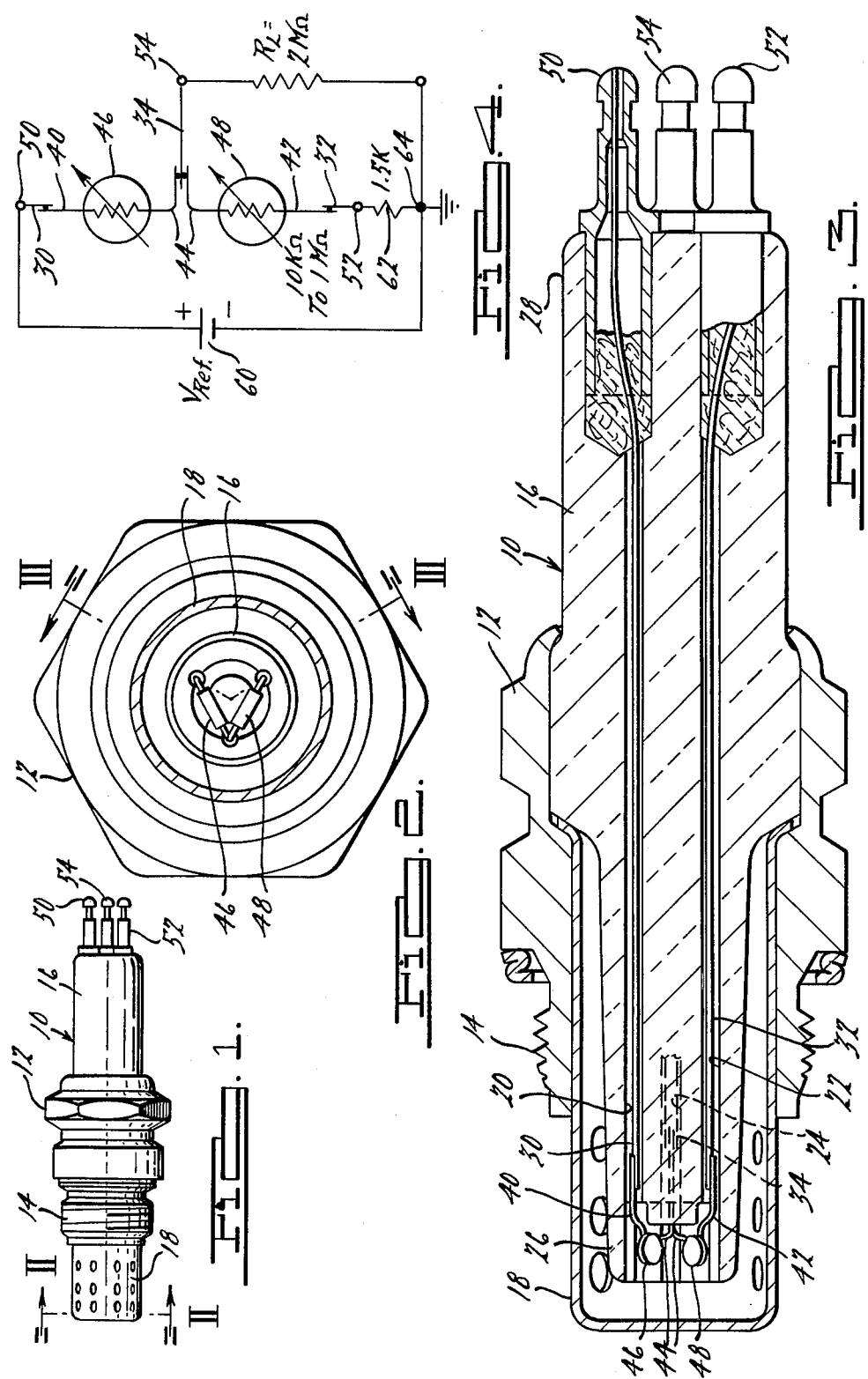

 (a)
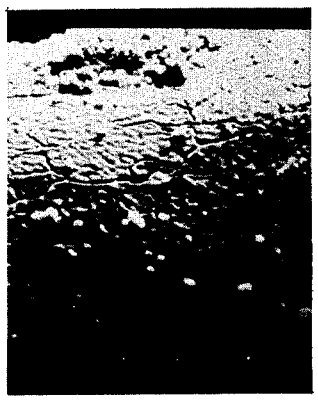 (b)
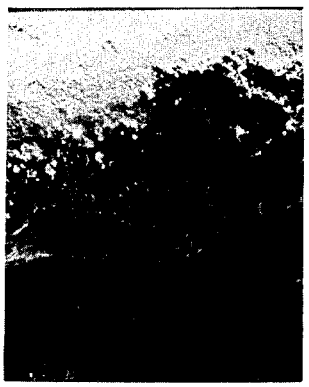 (c)
 (d)
FIG. 5.

(a)
(b)
(c)
(d)
FIG. 6.

EXHAUST GAS SENSOR ELECTRODE IMPROVEMENT

BACKGROUND OF THE INVENTION

This invention relates to an improved exhaust gas sensor of the type responsive to the partial pressure of oxygen in exhaust gases from an internal combustion engine. More specifically, the invention pertains to an exhaust gas sensor that uses titania or other ceramic elements to generate an electrical signal. The ceramic elements each have precious metal electrodes embedded therein for providing conductive electrical connection to the ceramic element. Resistance of the ceramic element varies as a function of the partial pressure of oxygen and/or temperature to which the ceramic element is exposed.

Exhaust gas oxygen sensors of this type are used in feedback fuel control systems for internal combustion engines. These fuel control systems utilize the step-function response of the sensor that results from similar step-function changes in the partial pressure of oxygen in the exhaust gases of an internal combustion engine as the air/fuel mixture supplied to the engine cycles between rich and lean with respect to the stoichiometric air/fuel ratio. In the titania exhaust gas sensor, the titania ceramic element has a low resistance when located in an environment containing a substantial amount of oxygen.

The preferred titania sensor consists not only of an element for measuring the partial pressure of oxygen, but also of a second element connected in series with the oxygen sensing element and used for purposes of providing temperature compensation of the sensor output voltage. In the preferred form, the oxygen sensing element is made from porous titania ceramic material and the temperature sensing element is a thermistor that may be made from a more dense titania ceramic material or from some other material such as praseodymium ferrite. The two elements typically are disc-shaped and each contains two precious metal electrode wires spaced apart from one another for use in measuring the electrical resistance between the electrode wires. The wires have in the past been made from pure platinum.

One of the failure modes of the exhaust gas sensors described above is due to degradation of the platinum electrode wires. The exhaust gas sensor in use is positioned in the exhaust system of an internal combustion engine. Usually the sensor is installed in an aperture at a location in the exhaust manifold near the flange that would connect to an exhaust pipe. The response of the metal oxide ceramic elements in the exhaust gas sensor to temperature and to the partial pressure of oxygen in the exhaust gases occurs over a normal temperature operating range that extends from about 350° C. to about 850° C. and which, in some cases, may extend from a lower temperature of 300° C. to a higher temperature of 900° C. The platinum electrode wires of the sensor are exposed to the exhaust gases and also are at temperatures within the ranges just mentioned. It is this hostile environment that produces the degradation of the platinum electrode wires of the prior art exhaust gas oxygen sensor.

According to the present invention, the durability of the platinum electrodes of an exhaust gas sensor is substantially improved.

SUMMARY OF THE INVENTION

In accordance with the invention, an improved sensor is provided designed for use in the environment of exhaust gases from an internal combustion engine. The improved sensor has at least one element made from a ceramic material that undergoes a change in an electrical characteristic thereof in response to a change in its temperature or to a change in the composition of the internal combustion engine exhaust gases to which the element is exposed when the element is at a temperature within the range from about 350° C. to about 850° C. The ceramic element has electrodes connected to it for use in detecting changes in the electrical characteristics of the element.

The sensor electrodes are improved to increase substantially their durability when exposed for long periods to exhaust gas compositions which are produced from the combustion of air/fuel mixtures either rich or lean with respect to stoichiometry. The improvement is accomplished by manufacture of the previous metal electrodes of the sensor from a material employing Pt as the major or only constituent thereof, except for impurities therein. The electrode wire material comprises Pt which, according to the invention, has reduced susceptibility to attack by carbon, under rich-mixture exhaust gas conditions, or to attach by oxygen, under lean-mixture exhaust gas conditions. This reduction in susceptibility to attack by carbon and oxygen is the result of fabricating the electrodes employing a method or means for increasing in magnitude the energy required to produce a chemical reaction between the platinum and carbon or oxygen in the exhaust gases.

Annealing the electrodes after their connection to, and fabrication of the ceramic element of the exhaust gas sensor increases the energy required for chemical reaction. Alloying the platinum electrode material with either gold or rhodium also increases this energy. Platinum/gold and platinum/rhodium alloys have both lower vaporization pressure and higher oxygen dissociation pressures than pure platinum. Moreover, the Pt/Au and Pt/Rh alloys, therefore, require more energy in order for a chemical reaction with carbon or oxygen to take place than of the alloy is the case with pure platinum, the vaporization pressure of the alloy being reduced in direct proportion to the amount of alloying element added to the platinum.

The invention may be better understood with reference to the detailed description which follows and to the drawings.

BRIEF DESCRIPTION OF THE DRAWINGS

FIG. 1 is an elevational view of a titania exhaust gas oxygen sensor suitable for installation in the intake manifold of an external combustion engine;

FIG. 2 is a sectional end view, taken along the line II—II in FIG. 1, of the sensor of FIG. 1 and is shown in enlarged scale;

FIG. 3 is a sectional view, taken along the line III—III in FIG. 2, showing the internal structure of the sensor of FIGS. 1 and 2 also on an enlarged scale;

FIG. 4 is a circuit diagram illustrating the manner in which the titania oxygen sensing element and the thermistor shown in FIGS. 1 through 3 are electrically connected with circuitry designed to receive the sensor output voltage;

FIG. 5($a$) is a photomicrograph, at 300 times actual size of a pure Pt wire electrode in the location at which the wire enters a titania porous ceramic oxygen sensing element;

FIG. 5(b) is a photomicrograph, at 1000 times actual size, of the upper surface of a portion of the Pt wire shown in FIG. 5(a);

FIG. 5(c) is a photomicrograph, at 300 times actual size, of the underside of a portion of the Pt wire shown in FIG. 5(a);

FIG. 5(d) is a photomicrograph, at 1000 times actual size, of the undersize of the portion of the Pt wire shown in FIG. 5(c);

FIG. 6(a) is a photomicrograph, at 1000 times actual size, of the Pt wire in its condition as received from the manufacturer and as incorporated in the titania oxygen sensing element prior to testing in an exhaust gas environment;

FIG. 6(b) is a photomicrograph, at 400 times actual size, of the Pt wire electrode at a location thereof that had been embedded within the titania oxygen sensing element during testing in an exhaust gas environment;

FIG. 6(c) is a photomicrograph, at 30 times actual size, of the Pt wire electrode in the portion thereof extending from a fracture location (on the left) to the point at which the wire enters the titania oxygen sensing element (on the right);

FIG. 6(d) is a photomicrograph, at 200 times the actual size, of the Pt wire electrode in the portion thereof immediately following its entry into the titania oxygen sensing element in which it had been embedded during testing in an exhaust gas environment;

DETAILED DESCRIPTION

Figure 7:
FIG. 7 is a photograph of the magnified end of an oxygen sensor having titania thermistor and oxygen sensing elements with embedded Pt/Au electrode wires fabricated according to the invention.

With particular reference now to FIGS. 1 through 3, wherein like numerals refer to like parts in the several views, there is shown a complete titania exhaust gas sensor assembly generally designated by the numeral 10. The sensor 10 includes a steel housing or body 12, which may be substantially identical to a typical spark plug body, having a threaded portion 14 for engagement with a suitable threaded aperture provided within the exhaust system of an internal combustion engine (not shown). In most cases, the sensor 10 would be installed in an aperture at a location in the exhaust manifold near the flange that would connect to an exhaust pipe. A ceramic insulator 16 extends through the body 12 and has a tapered portion 26 projecting outwardly from the body 12 into the volume defined by the boundaries of a perforated shield 18. There are three longitudinal passages 20, 22 and 24 extending from the projecting end 26 of the ceramic insulator to its opposite end 28. Wires 30, 32 and 34 are located in the respectively corresponding passages 20, 22 and 24 and are of a heat resistant character, preferably being made from an alloy such as 80% nickel- 20% chromium wire. These electrically conductive wires are welded to precious-metal electrode wires 40, 42 and 44, which are embedded in disc-shaped ceramic elements 46 and 48.

Element 46 is a ceramic titania $O_2$ sensor responsive to the partial pressure of oxygen in the gaseous medium to which this element is exposed. Sensor element 46 may be fabricated in accordance with the teachings of commonly assigned U.S. Pat. No. 3,886,785 issued June 3, 1975 and 3,932,246 issued January 13, 1976, both in the names of Stadler et al. With regard to the fabrication of the oxygen sensing element 46, it is suggested that consideration be given to the teachings of commonly-assigned and previously or concurrently-filed patents, relating to exhaust gas sensors or thermistors, expected to issue subsequent to the filing date of this application.

The element 48 is a thermistor. The thermistor may be made from titania ceramic material of greater density, near its theoretical density, than the density of the porous titania oxygen sensor 46. Alternatively, the thermistor 48 may be constructed in accordance with the teachings of copending and commonly assigned U.S. Patent Application Ser. No. 857,498 filed December 5, 1977, now U.S. Pat. No. 4,162,631, in the names of Logothetis, Laud and Park and entitled "Rare Earth-Yttrium, Transition Metal Oxide Thermistors". The thermistor 48 is intended to provide temperature compensation in accordance with the circuitry illustrated in FIG. 4 and is intended to be substantially nonresponsive to variations in the partial pressure of oxygen in the gaseous medium to which it is exposed.

The sensor of FIGS. 1 through 3 is intended to be used in conjunction with electronic circuitry for closed-loop feedback control of the amount of fuel supplied to an internal combustion engine. The sensor indicates whether the exahust gases contain a substantial amount of HC and CO or whether instead there is a substantial amount of oxygen, thereby, indicating whether or not the air-fuel ratio of the mixture supplied to the engine was rich or lean with respect to the stoichiometric value of about 14.7 parts of air to each of fuel by weight. This air-fuel ratio typically is expressed as a normalized air-fuel ratio lambda, wherein the actual ratio is divided by the stoichiometric value and the stoichiometric ratio therefore is represented as 1.0 in accordance with well known practice.

The exhaust gas sensor 10 has identical terminals 50, 52 and 54 designed for connection to external circuitry as specified above the enable it to be used in a feedback fuel control system. With particular reference now to FIG. 4, there is shown a circuit that schematically represents the manner in which the sensor 10 is utilized in association with such external circuitry. A DC source of regulated reference voltage 60 has its positive terminal connected to terminal 50 of the sensor oxygen responsive element 46. The lead wires 40, 42 and 44 from the sensor 46 and thermistor 48 are welded or otherwise joined, respectively, to lead wires 30, 32 and 34 to interconnect the two ceramic elements 46 and 48 as shown. The thermistor element 48 is connected through a response-shaping resistor 62 to ground potential at 64. The output voltage of the sensor 10 is taken between the sensor terminal 54 and ground potential. This signal is applied across the input impedance or load resistance $R_L$ (about two megohms) of the engine control electronic circuitry.

The input voltage to the circuit of FIG. 4 is obtained from the source reference 60 and is applied across the voltage divider comprising the series-connected variable resistances of oxygen sensor 46 and thermistor 48 is series with the response-shaping resistor 62. The output voltage is taken across the load resistance $R_L$.

The resistance values of both the oxygen sensor 46 and the thermistor 48 vary as a function of temperature and in the same direction, that is, the resistance of these elements decreases with increasing temperature. As a result, the voltage dividing effect provides an output voltage across the load resistance $R_L$ that is independent of temperature. The oxygen sensor 46, however, has a resistance which varies not only with temperature but also with the partial pressure of oxygen in the gaseous medium to which the sensor is exposed. An increase in the resistance of the oxygen sensor 46 causes the output voltage across the load $R_L$ to decrease, and a reduction in the resistance of the oxygen sensor causes a corresponding increase in the output voltage across the resistance $R_L$. Otherwise stated, an increase in oxygen content in the gaseous medium surrounding the oxygen sensing device 46 causes its resistance to increase in a manner hereinafter described and thereby causes a reduction in the voltage across the load resistance $R_L$. A decrease in the oxygen content of the gaseous medium causes the resistance of the oxygen sensor 46 to decrease in a corresponding manner and this causes an increase in the voltage across the load resistance $R_L$.

One of the failure modes of the exhaust gas oxygen sensor 10 is the fracture of the precious metal (platinum) electrode wires 40, 42 and 44 embedded in the titania oxygen sensing element 46 and the titania thermistor 48. These failures occur particularly with respect to sensor electrodes that have been exposed to exhaust gases that are hot and are produced from combustion of air/fuel mixtures rich of stoichiometry. The inventor has found this to be caused by attack of the Pt by reactive carbon deposited from the exhaust gases. If, however, the electrode wires are subjected to exhaust gases produced by lean air/fuel mixtures, Pt oxidation and consequential loss by vaporization contributes to the electrode material failure, especially at the higher operating temperatures of the element 46 and 48.

The composition of the exhaust gases from an internal combustion engine varies as a function both of the temperature of the exhaust gases and the composition of the air/fuel mixture supplied to the engine. The exhaust gases, contain hydrocarbons, carbon, carbon monoxide, oxygen, carbon dioxide, water and other components. The carbon, carbon monoxide and oxygen react reversibly to form carbon dioxide. At any given time and location within the exhaust system from the engine, the amount of these constituents varies as a function of the composition of the air/fuel mixture and the temperature at the particular location in question.

The exhaust gas sensor typically is positioned at a location in the exhaust system near the flange connecting the internal combustion engine's exhaust manifold to the exhaust pipe and ahead of any catalytic convertor or the like that might be used. The sensor 10 is exposed to hot exhaust gases that are cooling rapidly as they travel through the exhaust system. The exhaust gas sensor platinum electrode wires are subject to carbon attack when subjected to hot but cooling exhaust gases produced by combustion of a rich air/fuel mixture. Under this condition, the carbon, carbon monoxide and carbon dioxide equilibrium changes and is followed by the deposition on the electrode wires of reactive carbon, i.e., carbon in the form of fine particles.

The carbon attack of the platinum electrode wires of the prior art exhaust gas sensor is particularly pronounced at a temperature where the carbon deposition reaction is favored, i.e., in the exhaust environment mentioned above. The carbon is deposited on the platinum electrode wires of the sensor and forms platinum carbide ($PtC_2$). The reaction between the platinum and carbon occurs at the grain boundaries of the platinum due to the high energy concentrations at such locations. The $PtC_2$ formed at the preferred reaction site is a porous, flaky material that is electrically conductive at high temperature, but that is also brittle. The $PtC_2$ flakes off the Pt electrode wire, thereby, to expose fresh Pt to carbon deposition and further $PtC_2$ formation. In this way, the deterioriation progresses rapidly. The inventor has found that it is possible to duplicate the failure of sensor electrode wires due to carbon deposition and platinum carbide formation by exposing exhaust gas sensor electrode wires to a constant hot exhaust gas environment where the exhaust gases are produced by a natural gas burner apparatus supplied with a rich air/fuel mixture.

The text apparatus used was a natural gas burner having a long exhaust tube in which several exhaust gas sensors may be positioned. The burner is adapted to be supplied with controlled amounts of natural gas, either air or oxygen, and fuel additives used to simulate gasoline compositions. Test results using this burner have been verified in vehicle tests in that similar Pt electrodes have failed during testing of sensor which were abnormally exposed to rich exhaust gases for several hours.

FIGS. 5 and 6 pictorially illustrate the manner in which the formation of $PtC_2$ on a pure platinum electrode causes electrode wire deterioration as described above.

FIG. 6(a) illustrates a pure platinum wire (wire that is entirely platinum except for normal impurities and otherwise unalloyed) in the condition in which it was received from the manufacturer and incorporated in a titania oxygen sensing element prior to testing in a natural gas burner. It may be seen that the wire surface is quite smooth and free of surface defects.

FIGS. 5(a) and 5(b) show the surface of the platinum wire of FIG. 6(a) after the wire had been subjected to testing in the hot products of combustion of a rich mixture supplied by the natural gas burner. The wire had been in this exhaust gas environment for a period of less than seven hours. It is evident that the wire surface exposed to these exhaust gases has become cracked, grain boundaries have grown, and platinum carbide has been formed on the wire's surface resulting in its deterioration. The cracked grain boundaries and platinum carbide formations are more clearly shown in the photomicrographs, at 1000 times the actual size, of FIGS. 5(b) and 5(d). As the platinum carbide flakes shown in FIG. 5(b) are lost, a fresh platinum surface is exposed to the exhaust gas environment causing further formation of platinum carbide.

FIG. 6(c) is a photomicrograph at 30 times actual size, of the platinum wire electrode in its portion extending from a fracture location (on the left side of the photograph) to the point at which the wire enters the titania oxygen sensing element (on the right side of the photograph). This figure particularly illustrates the considerable deterioration of the platinum wire caused by hot exhaust gases produced from a rich mixture supplied to the natural gas burner.

FIGS. 6(b) and 6(d) illustrate the condition of the platinum wire in portions thereof that have been, during testing in the natural gas burner, located or embedded within the titania ceramic material. While these figures do show cracking of the platinum and some deterioration, there is little platinum carbide formation and the deterioration is not severe because these portions of the platinum wire had not been exposed to the same direct contact with the hot exhaust gases to which the wire portion exterior of the ceramic element was exposed.

Oxygen found in excess in exhaust gases produced by lean air/fuel mixtures also attacks the electrode material, particularly at temperatures of about 850° C. or higher. In such case, $PtO_2$ is formed and subsequently lost by vaporization. This phenomenon starts at lower temperatures, but does not become pronounced until higher temperatures are reached. Alloying gold or rhodium with the Pt electrode material increases the alloy material increases vaporization pressure and oxygen dissociation pressure.

It has been found that, in addition to the formation of $PtC_2$ and the loss of Pt by oxidation and vaporization, deterioriation of platinum wire electrodes occurs due to the presence of impurities in the precious metal from which the electrode wires are formed and also from stresses induced in the wire due to work hardening effects. The impurities can be controlled during manufacture of the wire and eliminate wire deterioriation from the reaction of these impurities with exhaust gas constituents, which constituents may include impurities in the fuel supplied to the burner. An example of this is the reaction formed between silicon or lead, present in the previous metal electrodes as an impurity, with sulphur contained as an impurity in the fuel supplied to an engine.

The deterioriation caused by stresses induced in the electrode wires may be relieved by annealing of the electrode wires in the completed sensor at a temperature in the range from about 900° to 925° C. or other suitable temperature for a time period sufficient to reduce the stresses in the electrode wires resulting from the oxygen sensor fabrication. The stress concentration induced by work hardening of the electrode material tends to increase the stored energy level of the electrode material. This assists in the formation of platinum carbide as discussed above and results in wire deterioriation. Therefore, one way in which the inventor has found to eliminate the deterioriation of exhaust gas sensor electrode wires is to anneal the wires to reduce the stresses induced in the exhaust gas sensor during its manufacture.

In addition to the above methods of reducing the formation of platinum carbide and subsequent deterioriation of exhaust gas sensor electrode material, it has been found that such $PtC_2$ formation may be substantially reduced by replacing the prior art pure platinum electrode material with a platinum alloy consisting essentially of platinum and a minor percentage of either gold or rhodium. The presently preferred composition of the electrode material is an alloy consisting essentially of 97.5% platinum and 2.5% gold by weight (hereinafter Pt/2.5Au). An alloy of about 95% platinum and 5% gold by weight also has been found to have substantially improved resistance to carbon attack as compared to the pure platinum material used in prior art practice. A lesser improvement in exhaust gas sensor electrode resistance to degradation from platinum carbide formation has been achieved by use of an electrode material consisting essentially of 87% platinum and 13% rhodium by weight (hereinafter Pt/13%Rh). The use, however, of a material consisting essentially of 90% Pt and 10% Rh by weight (hereinafter Pt/10%Rh) has been found to provide performance equivalent to that of the Pt/2.5%Au electrode material. From the standpoint of cost reductions of the exhaust gas sensor it may be desirable to fabricate the electrodes from a platinum alloy with gold or rhodium that is of a composition other than those previously mentioned. A Pt, Au alloy may contain gold in a percentage by weight extending from an excess of 0% to about 6%. The 6% limitation arises from the fact that gold-rich platinum alloy precipitates at about this composition due to its lack of complete miscibility in platinum. The gold-rich Pt alloy constitutes a second phase at the grain boundaries that increases the boundaries and subjects the electrode material to greater attack by carbon. Rhodium is completely soluble in Pt over the entire composition range. However, the amount of Rh alloyed with Pt is limited because increasing amounts of Rh increase the hardness of the alloy and it becomes more susceptible to work hardening. The Pt/Rh alloy is quite satisfactory up to an Rh weight content of 13%, but is of a more optimum composition of lower Rh concentration level is more desirable. Of course, the use of rhodium is some concentration greater than zero has been found to improve the resistance of the electrode wires to degradation by carbon attack. This occurs for reasons discussed further below.

Both gold and rhodium have lower vapor pressures than platinum and increase the oxygen dissociation pressure when added to platinum. The work associated with metal losses per unit area of the gas-metal interface is related to the heat of vaporization per unit volume. An increase in the magnitude of the heat of vaporization of the metal reduces its vaporization loss. Platinum alloyed with gold or rhodium has an increased magnitude in the alloy heat of vaporization as compared to the pure Pt.

Figure 8:
FIG. 8 is a photograph of the magnified end of an oxygen sensor having titania thermistor and oxygen sensing elements with embedded Pt/Rh electrode wires of the invention.

With particular reference now to the enlarged photographs of FIGS. 7 and 8, there is shown in FIG. 7 an end view of an exhaust gas sensor similar to the sensor 10 and having electrode wires 40, 42 and 44 (FIGS. 3 and 4) formed from a Pt/5%Au alloy composition. The sensor depicted in FIG. 7 has been subject to a hot exhaust gas environment from a natural gas burner operated with a rich air/fuel mixture for a period of 21 hours. The sensor electrode wires may be seen to be intact and of quite normal appearance. This is a substantial improvement over the results achieved with pure platinum electrode materials as previously described.

The FIG. 8 photograph illustrates an exhaust gas sensor similar to that shown in FIG. 7 and subjected to the same exhaust gas environment as was the sensor depicted therein. The FIG. 8 sensor electrode wires were formed from a Pt/10%Rh alloy composition. Similarly to the sensor of FIG. 7, the FIG. 8 sensor shows an electrode wire surface contour and integrity that is well-maintained even after the 21-hour exposure to the hot exhaust gases produced by combustion of a rich mixture.

Various tests have been conducted on sensors exposed to hot gases produced by rich mixture combustion. At about 780° C., carbon attack on pure platinum is very high and failure rates have been around 75% to 90% with respect to the electrode wires. It has been found that Pt/5%Au alloy as an electrode material is very stable in this environment and is slightly better in this respect than Pt/10%Rh, the latter having more grain growth than the former. However, it has been found that the Pt/10%Rh alloy has a considerably lower grain growth when exposed to the exhaust gas environment than does the Pt/13%Rh. Also it has been found that the homogeneity of the platinum/gold alloy has some importance with respect to the overall durability of the electrode wires.

In order to obtain the exhaust gas sensor electrode improvements of the invention, it is necessary to limit the impurities in the electrode material. Impurities in the electrode material segregate around the grain boundaries due to the thermal treatment of the electrode during use. Oxidation of impurity compounds results in formation of small cavities around the grain boundary. The growth of these cavities and their subsequent coalescence causes cracks to propagate along the grain boundaries. As the concentration of impurities increases, the total stress required for crack propagation through the grain boundaries decreases. Once the impurities start accummulating at the boundaries, the ductile-to-brittle transition temperature decreases and finally the fracture mode becomes intergranular. The grain boundary strength is inversely proportional to the impurity concentration.

The impurities in the electrode material may react with the constituents of the fuel supplied to the internal combustion engine or with other products of combustion included in the exhaust gases to which the electrode materials are exposed. Elements, such as phosphorus and sulphur, may cause temper-embrittlement in association with some alloying elements. In engine exhaust gases, sulphur and phosphorus compounds are in abundance and can be transported from the exhaust environment to the sensor electrodes via impurities like silicon, iron, lead, tin and zinc. These elements have high interaction energies for sulphur and phosphorus and accummulate at the grain boundaries with a large volume change. Under a varying concentration of oxygen in the exhaust gases, there is a preferential decomposition of the grain boundary compounds and this results in cavities being formed due to the volume change around the boundaries. The grain to grain coherence is severed and the subsequent coalescence of cavities accelerates crack propagation along the path of least resistance.

It has been found desirable to limit the impurity content of Pt/2.2% minimum by weight Au alloy electrode material, a currently preferred alloy, to no more than 100 parts per million and with no individual impurity element exceeding ten parts per million, except that silicon, lead, arsenic antimony and bismuth impurities are limited to a maximum of five parts per million and copper and silver impurities to one part per million each.

The data graphically depicted in FIGS. 13 to 16 of my commonly assigned, concurrently filed and joint U.S. patent application Ser. No. 5,425 entitled "Improved Ceramic Element Sensor" illustrates the benefits obtained with the present invention. This data was obtained during durability testing of exhaust gas sensors, having 97.5%Pt/2.5%Au electrode wires, which for 850 hours were subjected to exhaust gases produced by combustion of air/fuel mixtures cycling rich and lean of stoichiometry. There were no failures of sensor electrode wires.

Based upon the foregoing description of the invention, what is claimed is:

1. An improved exhaust gas sensor, the exhaust gas sensor having an element made from a ceramic material that undergoes a change in an electrical characteristic in response to a change in its temperature or in the composition of exhaust gases to which the ceramic element is exposed when at a temperature within the range from about 350° C. to about 850° C., the ceramic element having connected to it metallic electrodes employing Pt as the major or only constituent thereof except for impurities therein, the electrodes being used to detect changes in the electrical characteristic, wherein the improvement comprises:

the electrode material of the sensor comprising Pt having reduced susceptibility to attack by carbon deposited thereon from exhaust gases that are the products of combustion of an air/fuel mixture rich with respect to stoichiometry and to attack by oxygen in exhaust gases that are the products of combustion of an air/fuel mixture lean with respect to stoichiometry, such reduction being accomplished by employing in the fabrication of the electrodes a means for increasing in magnitude the energy required to produce a chemical reaction between the Pt therein and such carbon or oxygen in such exhaust gases.

2. An improved exhaust gas sensor according to claim 1 wherein such reduction of the susceptibility of the platinum in the electrode material to attack by carbon or oxygen is accomplished by alloying a second metal with the Pt metal of the electrodes.

3. An improved exhaust gas sensor according to claims 1 or 2 wherein such reduction of the susceptibility of the platinum electrode material to attack by carbon or oxygen is accomplished by annealing the electrodes after their connection to, and fabrication of, the ceramic element of the exhaust gas sensor.

4. An improved exhaust gas sensor according to claim 2 wherein the reduction in the susceptibility in the platinum material to attack by carbon or oxygen is accomplished by fabricating the electrodes from a material consisting essentially of Pt and a second metal selected from the group consisting of Au and Rh.

5. An improved exhaust gas sensor according to claim 4 wherein the electrodes are fabricated from a material consisting essentially Pt and Au, the Au being present in an amount less than that at which substantial presence of a second phase in the electrode material arises.

6. An improved exhaust gas sensor according to claim 5 wherein the gold is present in an amount greater than 0% and less than 6% by weight.

7. An improved exhaust gas sensor according to claim 6 wherein the Au is present in an amount between 2% and 5% by weight.

8. An improved exhaust gas sensor according to claim 4 wherein the electrodes are fabricated from a material consisting essentially of Pt and Rh.

9. An improved exhaust gas sensor according to claim 8 wherein the Rh is present in an amount greater than 0% and less than about 13% by weight.

10. An improved exhaust gas sensor according to claim 9 wherein the Rh is present in an amount of about 10% by weight.

11. An improved exhaust gas sensor according to claim 2 wherein the second metal alloyed with the Pt metal of the electrodes inhibits growth of the grains therein.

12. An improved exhaust gas sensor according to claim 11 wherein the impurity levels in the electrodes of the exhaust gas sensor are limited to specified amounts, thereby, to limit reaction of impurities in the exhaust gases with impurities in the electrodes and, thereby, to allow the second metal alloyed with the Pt metal of the electrode to inhibit the growth of grains therein.

* * * * *